United States Patent [19]

Nishino

[11] Patent Number: 4,676,786
[45] Date of Patent: Jun. 30, 1987

[54] PAPER DIAPER

[76] Inventor: Tetsuya Nishino, No. 4-16-3-607 Kyonancho,, Musashino City, Tokyo, Japan

[21] Appl. No.: 826,552

[22] Filed: Feb. 6, 1986

[30] Foreign Application Priority Data

Feb. 14, 1985 [JP] Japan .................................. 60-25177

[51] Int. Cl.⁴ ............................................. A61F 13/18
[52] U.S. Cl. ...................... 604/378; 604/382; 604/384; 604/385 R
[58] Field of Search ............... 604/358, 359, 378, 379, 604/380, 381, 382, 383, 384, 385 R

[56] References Cited

U.S. PATENT DOCUMENTS

| 3,017,304 | 1/1962 | Burgeni | 604/375 |
| 3,046,986 | 7/1962 | Harwood | 604/380 |
| 3,113,570 | 12/1963 | Holliday et al. | 604/370 |
| 3,124,135 | 6/1960 | Olson | 604/378 |
| 3,727,615 | 4/1973 | Duchane | 604/384 |
| 3,804,094 | 4/1974 | Manoussos et al. | 604/359 |
| 3,897,784 | 8/1975 | Fitzgerald | 604/380 |
| 4,061,785 | 12/1977 | Nishino et al. | 424/124 |
| 4,077,410 | 3/1978 | Butterworth et al. | 604/382 |
| 4,102,340 | 7/1978 | Mesek et al. | 604/381 |
| 4,103,062 | 7/1978 | Aberson et al. | 604/368 |
| 4,282,874 | 8/1981 | Mesek | 604/383 |
| 4,381,784 | 5/1983 | Aberson et al. | 604/378 |
| 4,480,000 | 10/1984 | Watanabe et al. | 604/378 |
| 4,559,051 | 12/1985 | Hanson | 604/378 |

Primary Examiner—C. Fred Rosenbaum
Assistant Examiner—Denise Whelton
Attorney, Agent, or Firm—Edward D. C. Bartlett

[57] ABSTRACT

A paper diaper comprises, from the top downwards, a fluff pulp surface layer or ply, a holed or grooved partition layer, a diffusion crust layer, and a fluff pulp main layer or ply, all wrapped up in a non-woven fabric. When the diaper is worn, fluid discharged is absorbed in a somewhat localized area, passes downwards through this area, and then falls down through the partition layer onto the crust layer which diffuses the fluid throughout substantially the whole area of the diaper and also retains some. Thus, the whole of the diaper is slightly moistened but does not cause any discomfort such as a drippingly wet feeling. Flowing back of the fluid from the crust layer to the surface layer is prevented by the partition layer.

14 Claims, 7 Drawing Figures

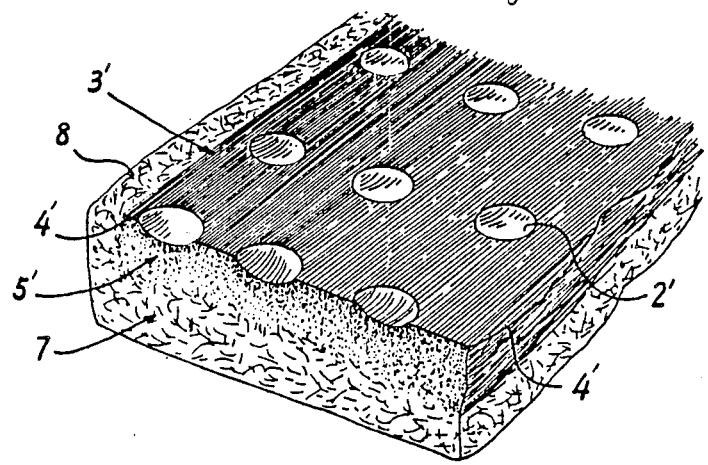
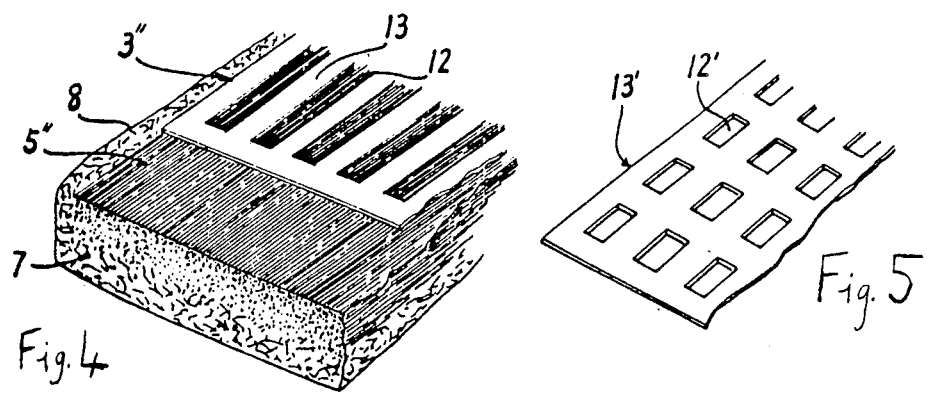
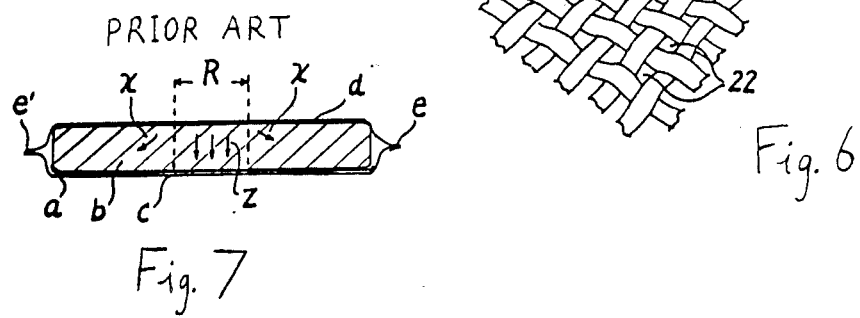

PAPER DIAPER

FIELD OF THE INVENTION

This invention relates to diapers for absorbing and retaining fluid such as urine, and particularly to paper diapers having fluff pulp as a primary element.

BACKGROUND OF THE INVENTION

Heretofore, many paper diapers have utilized fluff pulp for absorbing the fluid. FIG. 7 of the accompanying drawings illustrates a typical structure of a paper diaper of the prior art. In the diaper of FIG. 7, a fluff pulp layer "b" of a certain thickness is disposed on a suitable support paper "a", a vinyl sheet "c" covers underneath the support paper "a", and a non-woven sheet "d" is placed on top of the fluff pulp layer "b". Side edges "e" and "e'" of the diaper are heat sealed, and both ends in the longitudinal direction, that is the direction perpendicular to the sheet of the drawing, are also heat sealed to provide a finished product. As to specific shapes of the product, there are flat ones for the adult, folded ones to fit the groin to be fastened about the waist, or rolled up ones with side edges shrunk for infants.

The fluff pulp which is used as a principal material of such paper diapers is produced relatively at a low cost and is well accepted by the industry. However, it is a mass of short fibers with the fibers being little entwined with each other, so that it is unable to maintain a given shape and collapses easily. Since the fibers are not entwined in the fluff pulp, and there exists substantial gaps or clearance between the fibers, there is generated no capillary action and the fluid cannot be transferred throughout the mass of fluff pulp. Despite these shortcomings, fluff pulp is generally used as the principal element of a liquid or fluid absorbing diaper.

Applicant has observed closely the conditions of absorbing and retaining the excretion, particularly fluid such as urine, and referred to generally herein as the fluid, and realized there are several problems that must be settled. The discharged fluid passes through the external member, that is the non-woven fabric "d", which is in direct contact with a human body, to permeate and sink into the fluff pulp layer "b", but such permeation and sinking of the fluid is substantially confined or limited to a local area R enclosed by dotted lines in FIG. 7. This area R is coextensive with an area of the diaper where the fluid excreted from the human body makes contact with the diaper. Even if the fluid permeates and sinks into the thickness of the fluff pulp layer "b", there is no spreading of the fluid in the lateral direction "x" of the diaper. Likewise, there is no spreading of the fluid in the longitudinal direction. The fluid merely sinks down in substantially perpendicular direction "z" causing the fluff pulp to cave-in. When a large quantity of fluid is discharged locally, the area R cannot retain the fluid within itself, and part of the fluid penetrates to the surface of the vinyl sheet "c" at the bottom and starts flowing out therefrom over in internal surface of the vinyl sheet "c". Some portion of the fluid seeps along the fluff pulp surrounding, and in contact with, the vinyl sheet, but since the fluff pulp is unable to absorb the fluid by itself, the amount of the fluid that so seeps is limited; most of this fluid collects on the vinyl sheet surrounding the area R and leaks laterally towards the side edges. In order to prevent this lateral leaking, it will become necessary to perform additional steps, for example, to tighten that part of the diaper which contacts the groin into a cup-like shape, or to shrink the side edges. Such will merely increase the manufacturing cost while serving little purpose of dispersing or diffusing the fluid. Further, if the lateral leakage is prevented by means of the additional steps just described, the area R becomes a gorge of the diaper when worn by a person. The fluid collects in this gorge-like part in quantity and wets the area R drippingly while the fluff pulp outside the area R is not wet at all. This condition is felt by a wearer who feels discomfort in using the diaper. Thus, the fluff pulp, which has been prepared for the purpose of absorbing and retaining the fluid, actually causes this localized "fluid collection" which brings about a contrary effect of giving the wearer a thoroughly wet feeling. In addition, most of the remaining fluff pulp does not function to absorb and retain the fluid, which means a gross waste or uneconomical use of a significant amount of the material making up the diaper.

In order to try and improve the poor performance in absorbing and retaining the fluid when using fluff pulp, it has been proposed to use high polymer absorbing material together therewith. Referring to FIG. 7, the high polymer absorbent can be inserted between the support sheet "a" and the fluff pulp layer "b". Pulverized polymer contained in the high polymer absorbent has a high degree of hydrophilic property and is capable of absorbing an amount of fluid sixty times its own weight, having the characteristics of taking in the fluid while it swells and is gelled. However, since it does not possess the property of dispersing fluid, it cannot transfer the fluid laterally to the remaining dry polymer, even when the polymer under the area R is saturated with the fluid. It is not only incapable of solving the problem of local "fluid collection" in the fluff pulp, but also presents another problem of increasing the product cost since the high polymer absorbent is expensive.

SUMMARY OF THE INVENTION

This invention is concerned with solving or mitigating the problems of discomfort in use resulting from the wet feeling caused by localized fluid collection, waste or uneconomical use of raw material, and increase of manufacturing cost.

Accordingly, it is an object of the invention to provide a paper diaper which is pleasant to use yet inexpensive to manufacture, wherein the main element of the diaper is the fluff pulp, and substantially the whole of which is effectively utilized to maximise absorbtion and retention of the fluid.

Another object of the invention is to minimize the overall size of the diaper while obtaining effective fluid absorbtion and retention.

According to the present invention, a layer or ply of a paper diaper is pre-treated by adding a small amount of water, applying pressure in a given direction and heat drying the surface of a layer comprising a given thickness of fluff pulp in which the fibers are not entwined with each other but merely form a mass which easily collapses except the side edges. This pre-treatment causes pulp fibers near the surface, except the side edges, to be bonded together and aligned in a given direction, whereby a crust layer or ply having the strength not to collapse is formed continuously integral with a main body of fluff pulp underneath. This crust layer causes the fluid to be dispersed over a wide area by means of capillary action in the given direction, mainly the longitudinal direction of the diaper, the properties of the crust layer also enabling dispersed fluid to be retained therein. A non-water-absorbent or water resistant partition layer is provided on the crust layer integrally with or separately from the crust layer. This partition layer is provided with holes, grooves, slots, or the like punched or formed therethrough to allow the fluid to diffuse and fall down onto the crust layer. A thin fluff pulp surface layer or ply may be placed separately on the partition layer to prevent a rigid feeling or a wet feeling being caused by the partition layer to the skin of the user.

The fluff pulp of the surface layer or ply allows the fluid to permeate therethrough within a localized area, the crust layer under the partition layer diffuses and retains the fluid over a wide area, so that the diaper of the invention conveys to the user a soft touch without giving a wet feeling, and offers a pleasant feeling in use. The fluid, after passing through the fluff pulp of the surface layer or ply over a narrow area slightly wider than the local area where the fluid is discharged, passes through the holes or other openings in the partition layer to the crust layer. The crust layer exerts, by means of capillary action, its inherent diffusion and retaining properties over a much wider area to distribute and permeate the fluid in a small quantity per unit area to the main layer or ply of fluff pulp at both the forward and rear ends of the diaper. Thus, the fluid is caused to be dispersed and retained inside substantially the whole area of the diaper, allowing the diaper to be only slightly moistened throughout. There is no localized or concentrated collection of fluid at or in any of the partition layer, diffusion crust layer, or the lower main layer or ply of fluff pulp. The interior of the whole of the diaper may give the user a moistened feeling, however, the diaper does not convey any unpleasant drippingly wet feeling, and the edges or ears of the main layer or ply of fluff pulp at both sides of the crust layer effectively prevent lateral leaking of the fluid.

Other objects, features and advantages of the present invention will become more fully apparent from the following detailed description of the preferred embodiment, the appended claims and the accompanying drawings.

BRIEF DESCRIPTION OF THE DRAWINGS

In the accompanying drawings:

FIG. 3 is a fragmentary perspective view, similar to FIG. 2, of a second embodiment of the invention having a modified partition layer;

FIG. 4 is a fragmentary perspective view of a third embodiment of the invention having a separately formed partition layer;

FIG. 5 is a fragmentary perspective view of a further embodiment of a separately formed partition layer;

FIG. 6 is a fragmentary perspective view of yet a further embodiment of a separately formed partition layer; and FIG. 7 is a diagrammatic cross-sectional view across the width of a prior art paper diaper.

DETAILED DESCRIPTION OF THE PREFERRED EMBODIMENTS

Figure 1:
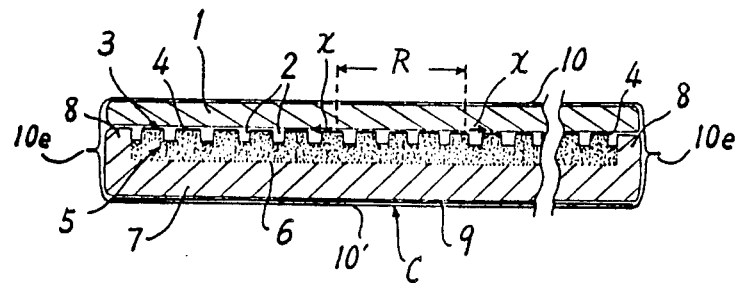
FIG. 1 is a diagrammatic cross-sectional view across the width of a basic embodiment of the paper diaper of the invention, a portion of the width being omitted for simplicity.
Figure 2:
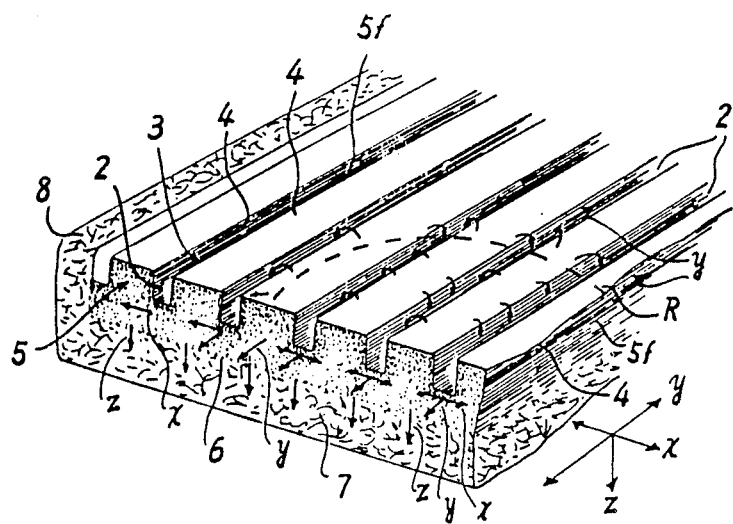
FIG. 2 is a fragmentary perspective view of a portion of a main part of the paper diaper of FIG. 1.

FIGS. 1 and 2 show a basic embodiment of the invention, FIG. 1 showing schematically a partial cross-section of the paper diaper of the invention, and FIG. 2 is a partial enlarged perspective view of the principal part of the paper diaper of FIG. 1.

The paper diaper of the invention comprises mainly a fluff pulp surface layer or ply 1 at the top; a partition layer 3, with openings, holes or the like therethrough, which is located under the surface layer and allows the fluid falling down from above to fall down to a lower layer without essentially absorbing the fluid; a crust layer 5 under the partition layer 3 which absorbs the fluid that falls down and disperses such fluid in an orientated manner, namely in lateral direction x but predominantly in longitudinal direction y (see FIG. 2); and a fluff pulp main layer or ply 7 inherently and integrally continuous to the crust layer 5, with the fluff pulp main layer 7 and the crust layer 5 being continuous at the lower face 6 of the crust layer as well as at both sides. Side edges of the fluff pulp main layer 7 form ears 8. Under the fluff pulp main layer 7, there is placed water resistant paper 9. The whole of the above components are wrapped in a non-woven fabric. In FIG. 1, upper and lower non-woven fabrics 10 and 10' are set together at side edges of the diaper, as shown at 10e, and heat sealed. Instead, it may be so arranged that one continuous sheet of non-woven fabric encloses the whole diaper with the edges heat sealed at one side edge or at the center C of the underside. Although not shown in the drawing, both ends in the longitudinal direction are similarly heat sealed to present a completed paper diaper.

Fluff pulp comprises a mass of short fibers, and since short fibers are not essentially entwined with each other, it is a mass that is fragile and collapsible. Such untwined fluff pulp fibers are piled together and compressed or the like to form a surface layer or ply 1 of suitable thickness in which short fibers are arranged tightly. It is preferable to place suitable deodorant or aromatic under the surface layer 1, or to mix the same in the lower portion thereof. The deodorant or aromatic may be, according to the invention, mixed into fluff pulp in pulverized form or by spraying or the like when the fluff pulp for the surface layer is caused to fall down from a loader to be piled. Any suitable odor improving agent may be used.

In making the crust layer 5, a belt-like body of fluff pulp of suitable thickness is placed on a belt, preferably air-permeable belt, air is sucked from below the belt to draw the piled fluff pulp down against the belt. Water in minute particles is applied to the upper surface of the belt-like body of fluff pulp by spraying or splashing, so that pulp fibers down to a certain thickness from the surface absorb water. This applying of water should be carefully executed to avoid cave-in of the fluff pulp, or penetration through the whole thickness of the piled pulp sheet due to wetting of a localized area. The thickness of piled pulp sheet that does not absorb water makes the fluff pulp main layer 7.

Next, pressure is applied to the upper surface of the fiber layer along substantially the longitudinal direction of the belt-like body of the fluff pulp in a longitudinal tangential direction to orient or align the fibers that absorbed water as much and predominantly as possible in the longitudinal direction. At the same time, this action causes the oriented fibers to bond tightly together leaving little gap or clearance between them. Then, by heat drying the fiber layer that absorbed water, the crust layer 5 is formed in which the fibers nearer to the surface are more closely bonded while maintaining their longitudinal orientation.

In the crust layer 5, the fibers, schematically shown in FIG. 2 as aligned fibers 5f, are caused to extend predominantly and substantially in the same direction, these fibers having minute gaps between each other. Thus the bonded aligned fibers will exhibit capillary action in the lengthwise direction y, and these fibers form an aggregated layer with sufficient strength, due to the bonding of the fibers, so that when fluid seeps in there will be no collapsing of the part that absorbs the fluid; such collapsing would occur if the fluff pulp fibers were simply unorientated and unentwined as in the prior art.

By adjusting the extent of application of the minute water particles to the surface of fluff pulp, as well as the degree of pressure applied, the thickness of the above crust layer and the degree of bonding and the orientation of fibers therein may be modified.

The lower part 6 of the crust layer 5, wherein the orientation and the degree of bonding are weak, is inherently continuous with the fluff pulp main layer 7. In the main layer 7, fibers are not entwined nor oriented. In FIGS. 1 and 2, the lower part 6 of the crust layer is shown by a dotted line for the sake of convenience, but in reality there is not any clear and definite demarcation between the lower part 6 of the crust layer and the main layer 7. The crust layer 5 is also integrally continuous, at both of its sides, to both side edges or ears 8 of the fluff pulp main layer 7.

In order to form the partition layer 3, openings or gaps are formed in the surface of the crust layer 5. These openings are created by forming, in the crust layer 5, a plurality of grooves 2 extending in the longitudinal direction. Grooves 2 may be formed by causing a roller having a plurality of annular rib-like protrusions to make contact with the surface of the crust layer to make parts of the surface corresponding to said protrusions cave in. Thereafter, a pharmaceutical, such as a water resistant agent or a water repellent agent, is applied in suitable manner to the remaining top protruding surface of the crust layer to provide a skin or film 4 which does not absorb water. The surface skin 4 extends between adjacent grooves 2. In FIG. 2 the film 4 is shown as something that is not transparent, but, in reality, it may be made transparent so that fibers arranged in the crust layer 5 may be seen therethrough. The grooves 2 are illustrated as being like square waves with sharp edges, but it will be understood that where grooves are made by pressing with a roller having rib-like protrusions, the edges and bottom of the respective grooves take on shapes that do not have sharply defined edges. Thus, the partition layer 3 is formed with a number of parallel grooves 2 extending in the longitudinal direction with film 4 located between the tops of the grooves. The film 4, which does not absorb water, is integral with the protruding upper surface of the crust layer 5, and repels the fluid falling down thereon so causing the fluid to fall down further into the grooves 2; this film 4 then seeps into the absorbent crust layer 5. The film 4 also functions to prevent the fluid which has seeped into the crust layer 5 and, subsequently, into the fluff pulp main layer 7 from flowing back upwardly to the surface layer 1, even when some pressure is applied thereto.

FIG. 3 is a partial perspective view of another embodiment showing another example of the partition layer in which a film 4', that does not absorb water, is attached integrally with the crust layer 5' in which many dimples 2' have been formed. The film 4' does not cover the concave surfaces of the dimples 2'. The film 4' is shown as a transparent element which allows the fibers of the crust layer to be seen therethrough.

Unlike the partition layers 3 and 3' integrally formed with the crust layer as explained above, it is possible to provide a partition layer separate from the crust layer. FIG. 4 shows such an example in a partial perspective view wherein the partition layer 3" comprises a water resistant sheet 13 made of paper, non-woven fabric, or the like to which a water resistant or water repellent process has been carried out. Openings 12 are formed through the sheet 13 by making longitudinal slots therealong, the slots being closed at each end. Water resistant sheet 13 is placed on the surface of crust layer 5".

As shown in FIG. 5, instead of slots, a water resistant sheet 13' having a number of windows 12' punched through it may replace partition layer 3" to be placed on the surface of crust layer 5". Each window 12' may be a circular, oval, or other shaped hole.

As a separate partition layer, an open woven fabric 23, like a net, as shown in FIG. 6, on which a water resistant or water repellent process has been carried out, may be employed. The fluid passes through interstices 22 of the net, is dispersed thereby and falls down onto the crust layer 5, 5' or 5" upon which the net is supported.

In the above embodiments, crust layers 5' and 5" are manufactured similarly to crust layer 5, and similarly integrally merge into the main fluff pulp layer 7.

Now, fluid absorbing and retaining action of the paper diaper of the invention will be explained. Referring to FIGS. 1 and 2, discharged fluid passes through non-woven fabric 10 and fluff pulp surface layer 1 within the area R and reaches the partition layer 3. Since fluff pulp surface layer 1 is a mass of short fibers not entwined, the fluid does not stop in the surface layer 1, but soon reaches the apertured partition layer 3 and falls into holes, gaps or grooves therebelow. Thus, fluff pulp surface layer 1 in contact with human body does not convey a wet feeling, namely does not give an unpleasant feeling. Further, the surface layer 1 serves as a buffer means to convey to the skin a feeling of soft touch.

The fluid that reaches onto the impervious film 4 of the partition layer 3 cannot be absorbed and spreads in the longitudinal direction, shown by the arrows y in FIG. 2, on top of the film 4; while some of the fluid spreads in the lateral direction shown by the arrows x and drains or falls through the apertures of the film 4 into the grooves 2 below, and then seeps into the crust layer 5 through the locations or areas between the sides of the grooves. Once the fluid seeps into the crust layer 5, the fluid is prevented from flowing backward (i.e. upwards) by the partition layer 3. The crust layer 5, which exhibits capillary action predominantly in the longitudinal direction y, draws the fluid mainly in the longitudinal direction while drawing some portion in the lateral direction x, thus causing the fluid to be dispersed in both longitudinal and lateral directions, namely throughout the entire area of the paper diaper. The crust layer 5 does not only diffuse the fluid, but also is capable of retaining a substantial amount of fluid in itself.

When the fluid, which has been diffused and retained over a wide area of the crust layer in the manner described above, can no more be retained in the crust layer, the fluid seeps into the fluff pulp main layer 7 as indicated by the arrows z in FIG. 2. Penetration of the fluid in the z direction does not take place just within localized area R as explained in connection with the known article shown in FIG. 7, but instead takes place at many places over the wide area of the entire diaper. Consequently, the amount of fluid that seeps into the main layer 7 in this way is small per unit area. Because of this, the fluid is prevented from penetrating only a certain local area of the fluff pulp layer 7 to collect at the bottom thereof, and the entire thickness of the fluff pulp main layer 7 both in longitudinal and lateral directions is evenly moistened by a small amount of the fluid. Thus, the uneconomical defect of known diapers in which most of the main layer in the longitudinal direction, except for the localized area R, remains dry without absorbing the fluid is avoided, and the fluff pulp main layer 7 is effectively utilized by the present invention. Water repellent paper 9 performs the primary function of supporting the main layer 7, which is slightly and evenly moistened all over as described above, and does not work like a saucer to collect the fluid penetrating through, and falling down from, the main layer 7. Therefore, that which supports the bottom of the water repellent paper 9 need not be a vinyl sheet as in the prior art, but direct wrapping with a non-woven fabric 10', which is advantageously gentle to the skin, can be effectively employed.

However, for the sake of safety, a vinyl sheet may be employed if desired.

The ears 8, at both side edges of the fluff pulp main layer 7, stop spreading out of the fluid in the lateral direction x beyond the edges of the partition layer 3 and diffusion crust layer 5. Since the ears 8 contain a mass of fibers not entwined, there is no diffusion and transfer of the fluid, so that the fluid does not seep or leak out laterally. Ears 8 also serve as a buffer when the diaper is applied to a person's body, making the diaper more comfortable to wear.

As will be realized, the invention has the effect as follows: the discharge is widely diffused and distributed over the entire area of the diaper, so that maximum overall effective utilization of the main absorbent material is realized, without giving a dripplingly wet feeling to a user even when more fluid than previously possible is absorbed; and if the diaper is to be changed when the same volume of discharge fluid as before (i.e. with known diapers) is excreted, the size of the diaper may be made smaller so improving the feeling when the diaper is strapped on the user. Since edges of the fluff pulp of the primary element of the diaper can completely prevent lateral spread and leakage of the fluid, complex additional manufacturing processing, such as shrinking or rolling of the part of the diaper in contact with the groin, may be omitted, and the use of expensive material such as high polymer absorbent is not necessary so that the manufacturing costs can be reduced.

In summary, the paper diaper of the invention does not bring about a concentration of fluid collection, and the fluff pulp main layer adjacent to the skin is not noticeably wetted, and gives a dry and soft feeling to the user which is effective in giving a pleasant feeling in use.

The above described embodiments, of course, are not to be construed as limiting the breadth of the present invention. Modifications, and other alternative constructions, will be apparent which are within the spirit and scope of the invention as defined in the appended claims.

What is claimed is:

1. A paper diaper, comprising:
    a surface layer of fluff pulp in which fibers thereof are not entwined but are aggregated together;
    a partition layer having spaced-apart openings therein and being located under said surface, said partition layer being non-absorbent but said openings allowing fluid to fall down therethrough;
    a crust layer comprising fluff pulp fibers which are oriented in a longitudinal direction of the paper diaper and are bonded to each other, said crust layer being disposed under said partition layer to receive and diffuse in an oriented manner the fluid falling down through the openings in said partition layer and to retain at least some of the fluid;
    a fluff pulp main layer disposed under said crust layer and comprising fluff pulp fibers which are not essentially entwined and bonded to each other;
    said main layer having upstanding peripheral edge portions between which said crust layer is disposed;
    said main layer being integrally continuous with a lower part of said crust layer and said upstanding peripheral edge portions being integrally continuous with edge portions of said crust layer;
    said crust layer being enclosed by said partition layer, said upstanding peripheral edge portions and said main layer; and
    an outer covering enclosing said layers.

2. The paper diaper of claim 1, wherein said partition layer comprises a plurality of grooves in a top surface of said crust layer and extending in a longitudinal direction of the diaper, and a fluid resistant covering over the top surface of said crust layer between said grooves.

3. The paper diaper of claim 1, wherein said partition layer comprises a plurality of cavities dented into a top surface of the crust layer, and non-absorbent film covering said top surface except where said cavities are disposed.

4. The paper diaper of claim 1, wherein said partition layer comprises a water resistant layer separate from the crust layer and placed on a top surface of the crust layer.

5. The paper diaper of claim 1, wherein an odor improving agent is mixed in the lower part of the fluff pulp making up the surface layer.

6. The paper diaper of claim 5, wherein said agent is a deodorant.

7. The paper diaper of claim 5, wherein said agent is an aromatic.

8. The diaper of claim 1, wherein said partition layer comprises a fluid resistant coating on said crust layer.

9. The diaper of claim 1, wherein said partition layer comprises an open woven fabric, said openings being formed by interstices between woven elements of the fabric.

10. The diaper of claim 1, wherein said partition layer comprises a fluid impervious film extending over said crust layer.

11. A diaper, comprising:
    a surface layer of fluff pulp;

a partition layer having a plurality of openings therethrough, said partition layer being disposed below said surface layer;

a crust layer comprising fluff pulp fibers which are oriented and bonded together, the crust layer being disposed beneath said partition layer;

a fluff pulp main layer below said crust layer;

an outer covering enclosing said layers;

said surface layer comprising fluff pulp fibers which are compacted together;

said crust layer orientated fibers being orientated in a lengthwise direction of the diaper;

said crust layer having grooves in a top surface thereof, said grooves extending lengthwise in said lengthwise direction and extending downwardly only partway through said crust layer;

said partition layer comprising a fluid resistant coating on said top surface of said crust layer between said grooves, said openings extending in said lengthwise direction in register with said grooves;

said main layer comprising fluff pulp fibers which are not entwined and not bonded together;

said main layer being integrally continuous with a lower part of and with side edges of said crust layer;

upstanding edge portions of said main layer enclosing the side edges of said crust layer;

said outer covering comprising non-woven fabric extending over upper and lower surfaces of the diaper; and an odor improving agent being disposed in a lower portion of said surface layer adjacent said partition layer.

12. A diaper, comprising;

an upper layer of fluff pulp through which fluid can freely pass downwards;

a partition layer below said upper layer, said partition layer preventing passage of the fluid therethrough except through openings in the partition layer, said openings being spaced apart and distributed over the partition layer;

a body of fluff pulp below said partition layer;

said body having an integral top crust layer juxtaposed said partition layer, said crust layer having fluff pulp fibers oriented in a longitudinal direction of the diaper and bonded together to enable the fluid passing downwards through said openings to be absorbed in said crust layer and seep throughout said crust layer in said longitudinal direction by capillary action;

said crust layer having depressions in a top portion thereof extending downwardly from a top surface thereof and only partway through said crust layer;

said depressions being in register with said openings; and said body of fluff pulp having upwardly extending peripheral edge portions extending parallel to said longitudinal direction and enclosing side edges of said crust layer to minimize lateral leakage from said side edges of the fluid absorbed in said crust layer.

13. The diaper of claim 12, wherein:

said upper layer is compressed and fibers thereof are arranged tightly; and said partition layer comprises a fluid resistant coating on said top surface of said crust layer and extending over said top surface between said openings.

14. A diaper for absorbing fluid, comprising:

a surface layer of fluff pulp which is compressed and in which fibers thereof are not entwined but are arranged tightly together, said surface layer allowing the fluid to pass downwardly therethrough;

a partition layer located under said surface layer, said partition layer having a plurality of spaced-apart openings therethrough and distributed thereover, said partition layer preventing passage of the fluid therethrough except through said openings;

a crust layer comprising fluff pulp fibers which are orientated in a longitudinal direction of the diaper and bonded together, said crust layer being disposed under said partition layer to receive and diffuse throughout said crust layer the fluid passing through said openings and to retain at least some of this fluid;

a fluff pulp main layer below and on opposite sides of said crust layer, said main layer comprising fluff pulp fibers which are not essentially entwined and bonded together, and said main layer being integrally continuous with a lower part and side edges of said crust layer;

said main layer having upwardly extending edge portions which bound and enclose said side edges of said crust layer and minimize seepage of the fluid from said side edges;

the fibers of said crust layer having weak orientation and bonding at a bottom portion of said crust layer where said crust layer blends into said main layer;

said partition layer comprising a transparent film of water resistant material coated on an upper surface of said crust layer and extending thereover between said openings;

said crust layer having spaced-apart depressions in said upper surface, said depressions underlying said openings to receive the fluid passing downwardly through said openings and said depressions extending downwardly only partway through said crust layer;

an odor improving agent adjacent a bottom of said surface layer;

a layer of water resistant paper under said main layer;

an outer covering of non-woven fabric enclosing said surface layer, said main layer, said crust layer, and said paper layer; and said partition layer, said crust layer, and said main layer interrelating to cause the fluid absorbed by the diaper to be diffused over a wide area of said crust layer with a substantial amount of the fluid being retained in said crust layer, any fluid said crust layer is not able to retain being distributed throughout said main layer which then becomes evenly moistened.

* * * * *